United States Patent [19]

Malis

[11] 4,196,966

[45] Apr. 8, 1980

[54] BINOCULAR MAGNIFICATION SYSTEM

[76] Inventor: Leonard I. Malis, 219-44 Peck Ave., Hollis Hills, N.Y. 11423

[21] Appl. No.: 901,486

[22] Filed: May 1, 1978

[51] Int. Cl.² .................. G02B 23/02; G02B 27/14
[52] U.S. Cl. ..................................... 350/145; 128/23; 350/171; 362/32; 362/804
[58] Field of Search ................. 128/23; 350/145, 171, 350/174; 362/32, 804

[56] References Cited

U.S. PATENT DOCUMENTS

| | | | |
|---|---|---|---|
| 3,586,414 | 6/1971 | Schultz | 350/145 |
| 3,589,799 | 6/1971 | Hotchkiss | 351/16 X |
| 3,745,993 | 7/1973 | Feinbloom | 128/33 |

OTHER PUBLICATIONS

The Xonix Stereoscope (advert.); *American Journal of Ophthalmology;* May, 1971, 350/145.

Keeler (advert.), *American Journal of Ophthalmology;* May, 1971, 350/145.

*Primary Examiner*—John K. Corbin
*Assistant Examiner*—Scott J. Sugarman
*Attorney, Agent, or Firm*—Kenyon & Kenyon

[57] ABSTRACT

Binocular magnification, and magnification and illumination apparatus are disclosed. The apparatus is lightweight and mounted on a head harness, and is especially suited for use by surgeons. In a disclosed embodiment, the apparatus combines Galilean-type binocular telemicroscopes and fiber optic illumination. A periscope-type reflection system provides axes of vision having a spacing less than the interocular distance. The axes of vision from the apparatus form a small angle within which the axis of illumination is projected. The apparatus provides stereoscopic vision and projects illumination through small openings or in or along passageways having an inside dimension of less than about 1½ inches.

11 Claims, 10 Drawing Figures

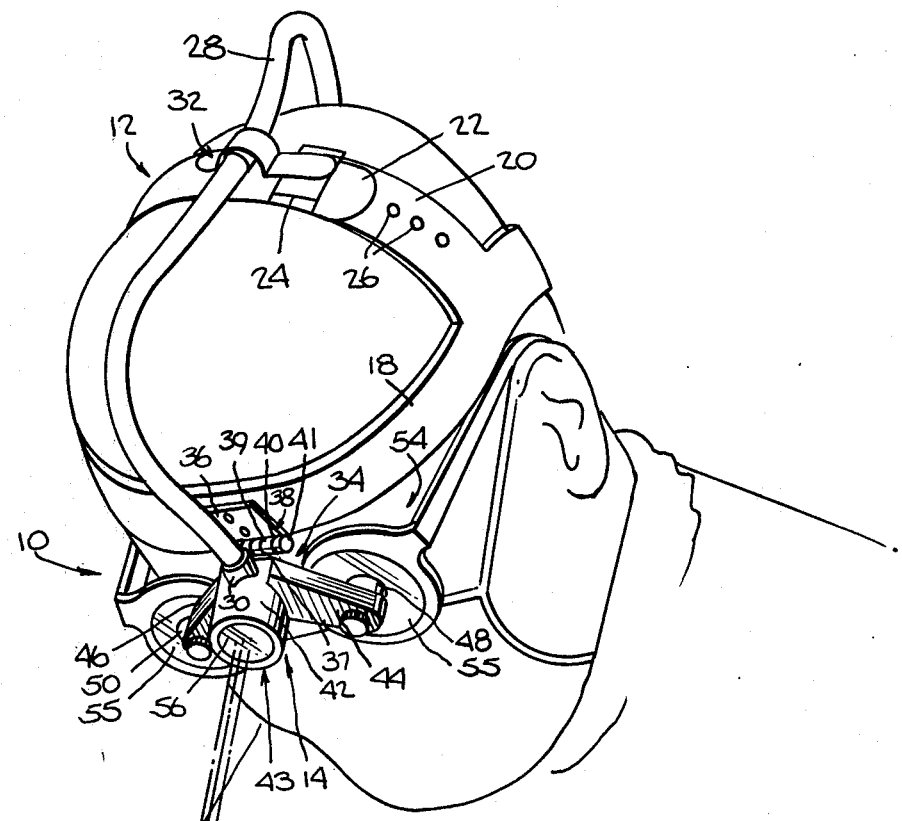
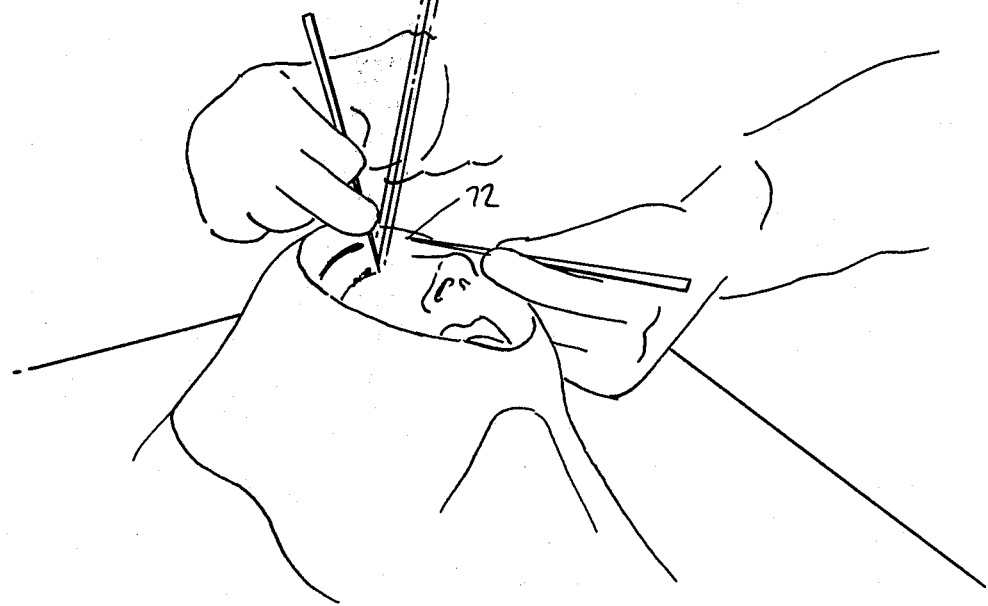
Fig. 1.

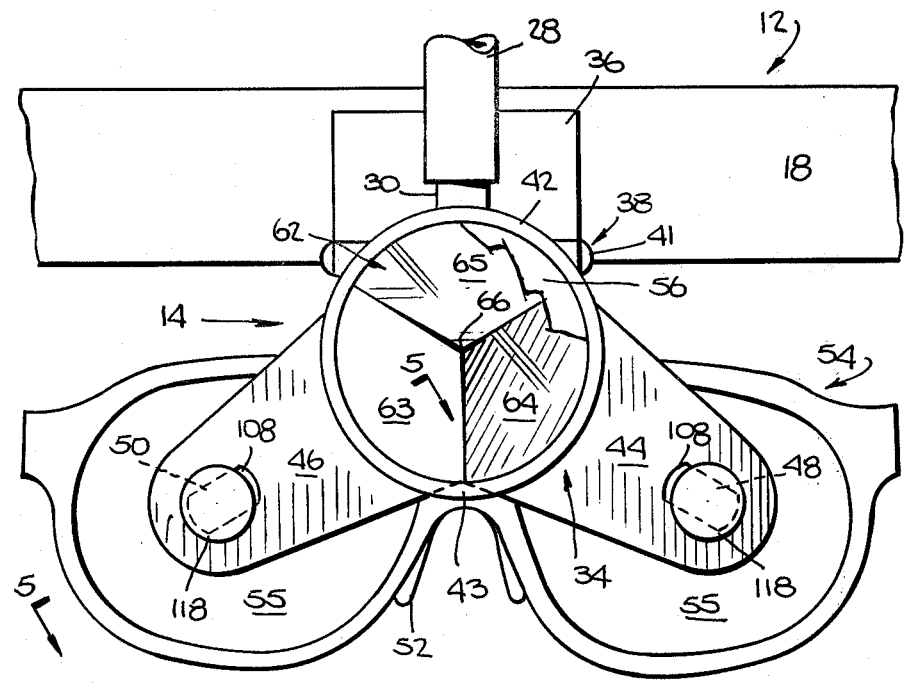
Fig. 2.
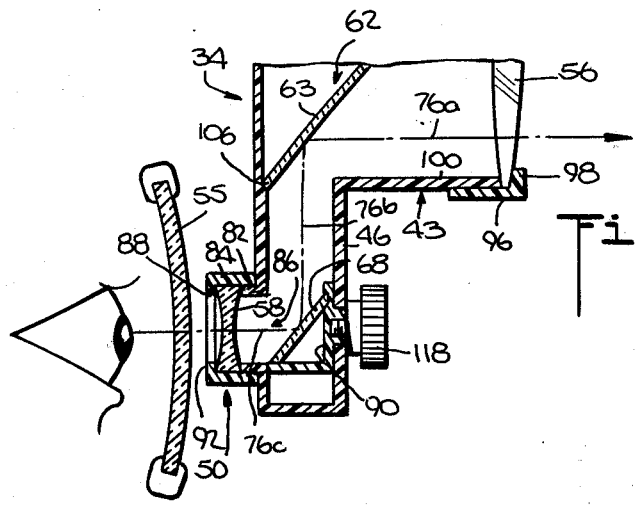
Fig. 5.
Fig. 6.
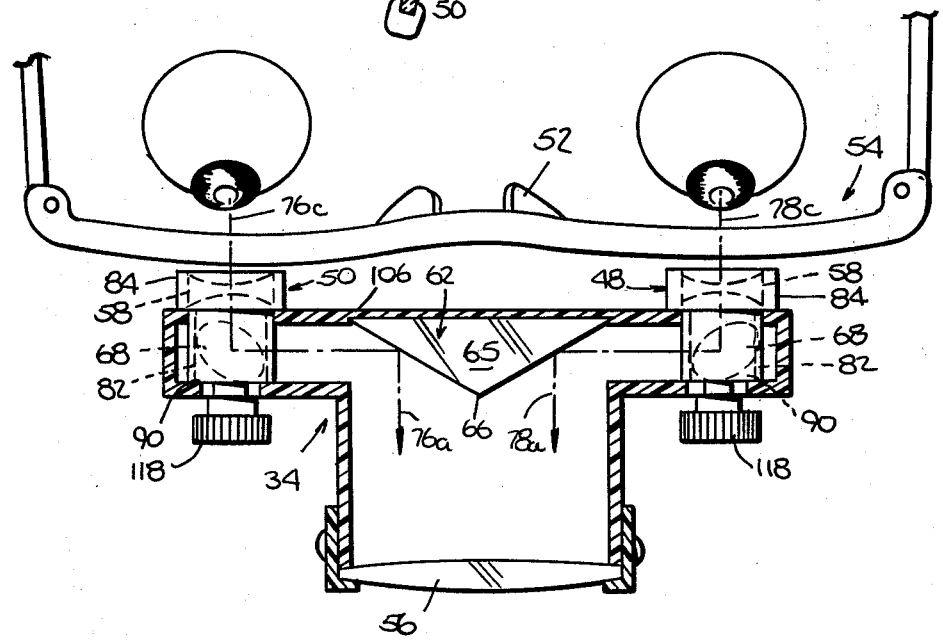

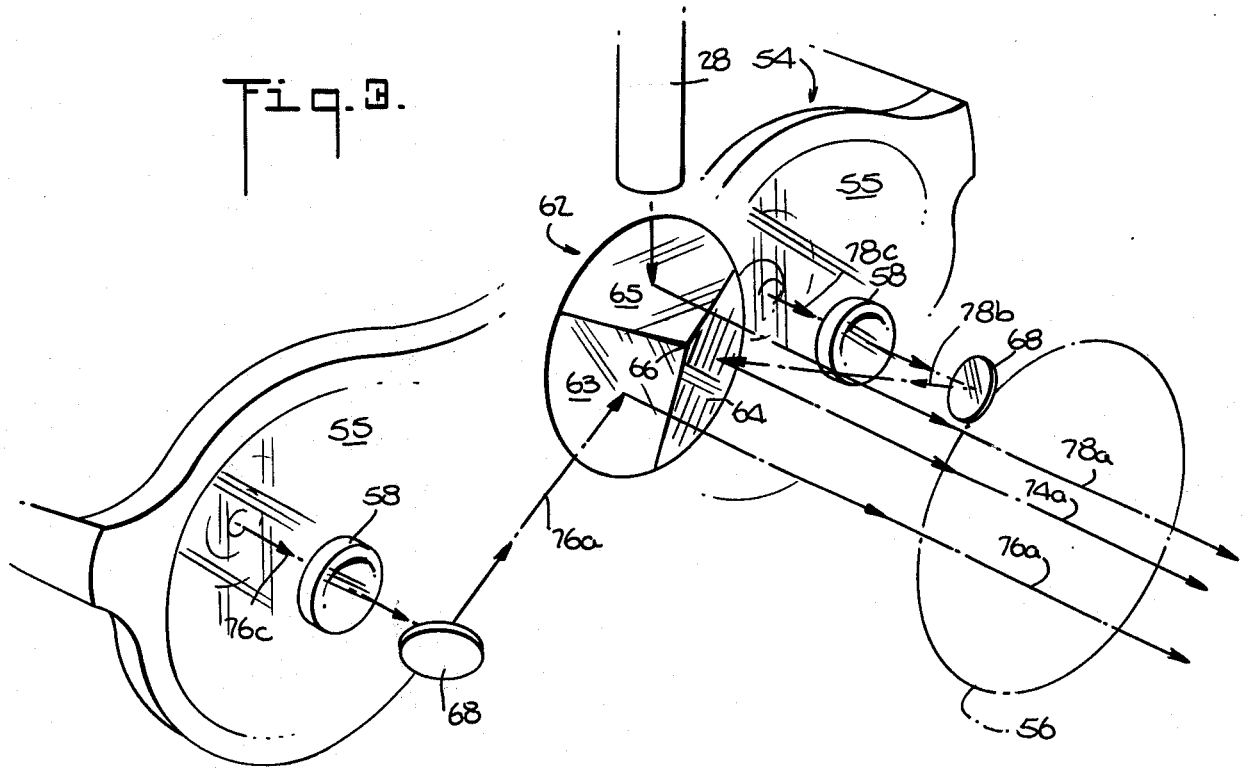
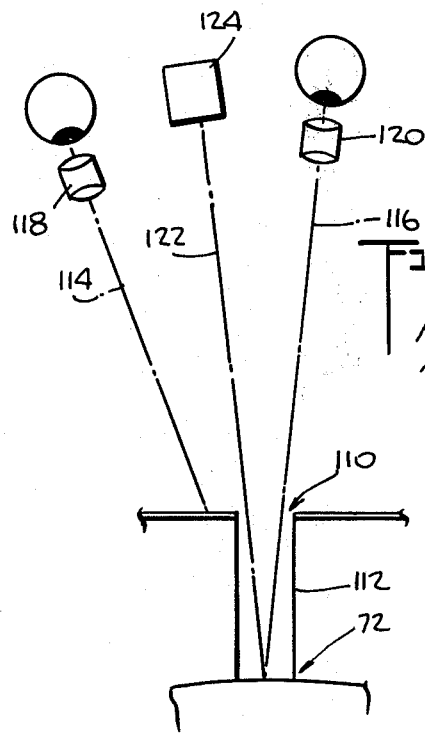
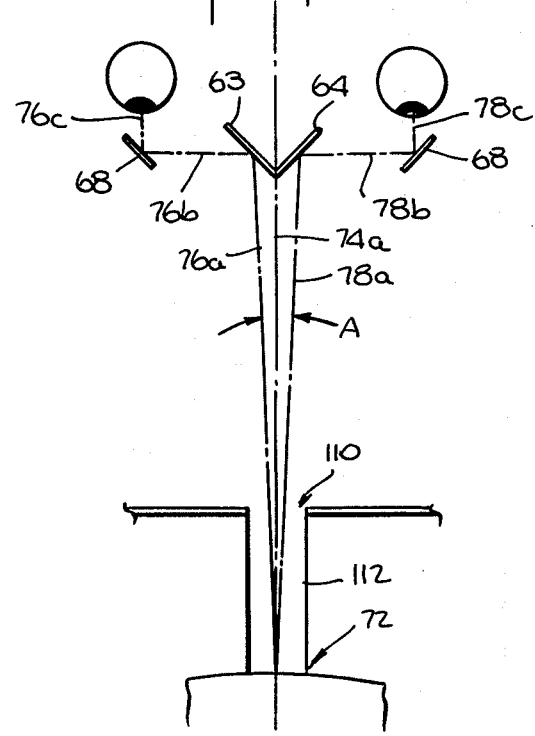

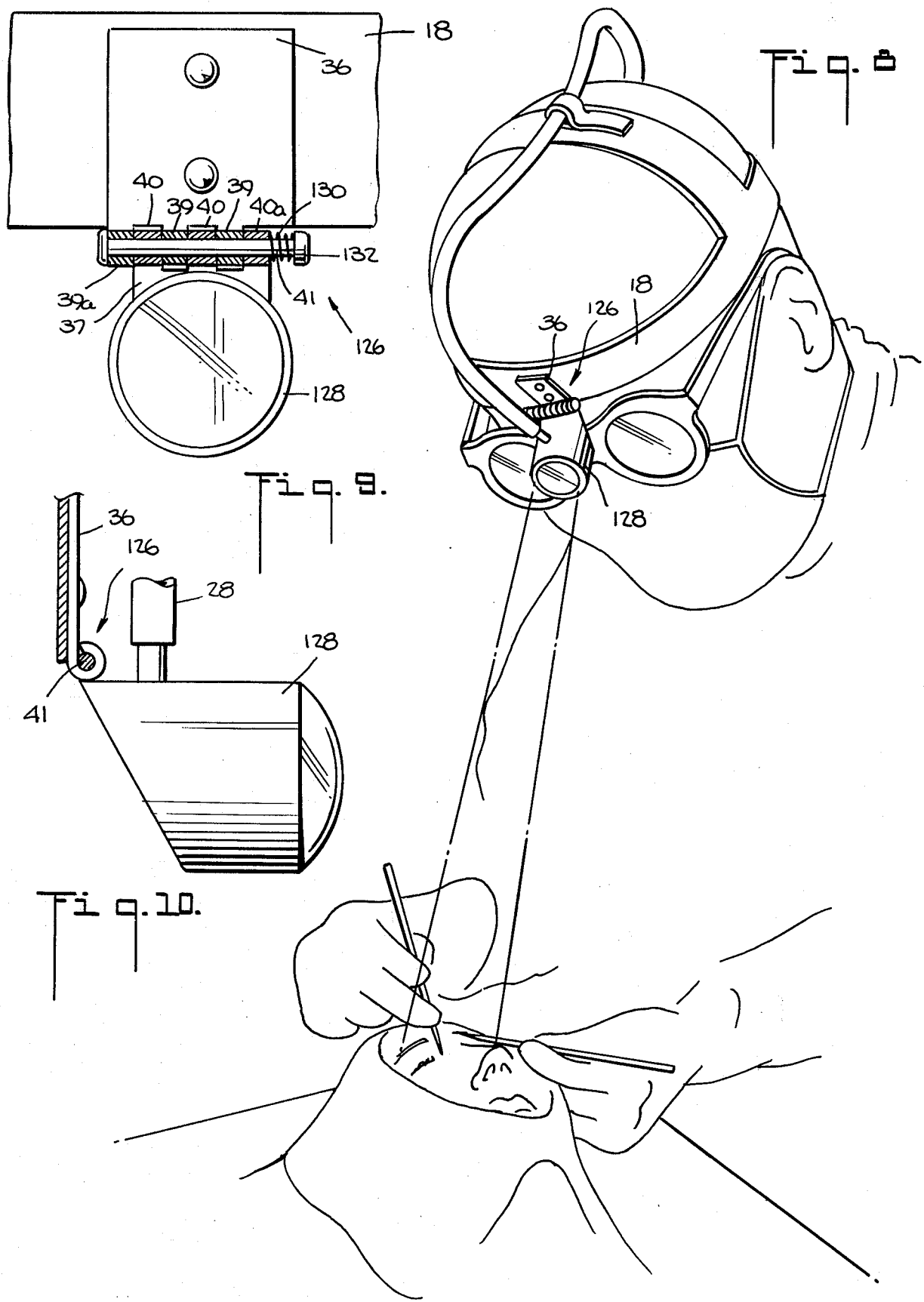

BINOCULAR MAGNIFICATION SYSTEM

BACKGROUND OF THE INVENTION

The present invention relates to binocular stereoscopic magnifying systems and to combined illumination and binocular stereoscopic magnifying systems. More particularly, the present invention relates to such systems which are worn on the head and are particularly suited for use by surgeons.

It is difficult for human eyes to observe a small object located beyond a small opening, or in or at the end of a narrow passageway. When the object is brought close enough to see it clearly, there may be problems with stereoscopic focusing through the opening or along the narrow passageway using both eyes. Use of one eye to obtain a satisfactory focus has the disadvantage of loss of depth perception. When the object is sufficiently spaced from the eyes to provide a satisfactory stereoscopic focus, visual acuity is diminished. Thus, stereoscopic focus and visual acuity are competing factors. When it is necessary or desirable to illuminate the object being viewed by projecting illumination through the opening or narrow passageway, additional problems are presented.

The aforementioned problems exist particularly in the surgical field where the surgeon must position himself sufficiently distant from the operating area to enable him to operate while being sufficiently close thereto to enable him to clearly see the operating area. This distance may place the surgeon's eyes in the range of from about 5 inches to about 30 inches, usually from about 8 inches to about 20 inches, from the operating area. In these ranges, the aforementioned problems of visual acuity and easy stereoscopic focus exist, particularly for small objects located beyond small openings or in or at the end of a narrow tube or passageway. For neurosurgeons, the problem becomes acute when operating in or through a nasal passage or auditory canal, for example. Individual surgical telemicroscopes and eye loupes worn by the surgeon are not entirely satisfactory in that it is still difficult to obtain stereoscopic vision and depth perception, particularly through small openings or in or at the end of narrow passageways. Operating room microscopes may be used. However, they are large and bulky, and are burdensome to use, move and adjust. They also restrict the surgeon's mobility and may cause eye fatigue during long periods of use. There also exists the additional problem of projecting illumination through small openings or along narrow passageways to the operating area and at the same time viewing the area. Conventional fiber optics head lamps used with eye loupes are also not satisfactory not only because of the difficulty in stereoscopically viewing the operating area as described above, but also because it is extremely difficult to maintain illumination on the operating area and a stereoscopic focus with even the slightest movement of the surgeon's head. Such eye loupes are positioned adjacent each eye of the surgeon and are consequently relatively widely spaced, with the minimum spacing being determined by the interocular distance of the particular surgeon. The optical axis of the fiber optics head lamp is located between the axes of the loupes. A wide angle of convergence is thereby formed between the widely spaced optical axes of the loupes and the surgeon must precisely position himself to locate the convergence point through the small opening or in the narrow passageway while providing a path of vision for each eye which is not blocked by the edges of the opening or sides of the passageway. Slight movement of the surgeon's head may result in the path of vision to one of the eyes being blocked by the edges of the opening or sides of the passageway. This makes it extremely difficult to both illuminate and view with both eyes a small object or operating area located beyond a small opening or in or at the end of a narrow passageway using known systems of the type described.

The invention disclosed herein overcomes the aforementioned drawbacks and provides improved binocular stereoscopic magnifying apparatus and combined binocular stereoscopic magnifying and illuminating apparatus.

SUMMARY OF THE INVENTION

It is an object of the present invention to provide apparatus for binocular stereoscopic magnification having improved stereoscopic focusing and visual acuity.

It is another object of the present invention to provide apparatus for binocular stereoscopic magnification and illumination having improved stereoscopic focusing, visual acuity and illumination.

It is yet another object of the present invention to provide apparatus for binocular stereoscopic magnification of an area or object located beyond a small opening in or at the end of a narrow passageway.

It is also an object of the present invention to provide apparatus for binocular stereoscopic magnification and illumination of an area or object located beyond a small opening or in or at the end of a narrow passageway.

It is a further object of the present invention to provide improved mountings for head-worn magnification and illumination apparatus and particularly for a head-worn illumination apparatus.

These and other objects are achieved by apparatus according to the invention in which the axes of vision thereof to the viewing area have a spacing which is less than the interocular distance, i.e., the spacing of the optical axes from the eyes to the viewing area is reduced. Additionally, illumination is projected towards the area along an optical axis which is located intermediate the axes of vision from the apparatus to the area. The improved mounting includes a hinge which is spring tensioned to allow continuous angular adjustment of the apparatus or surgical head lamp by overcoming the spring tension.

According to the invention in a disclosed embodiment thereof, a binocular stereoscopic magnification system is provided comprising first and second spaced viewing means having first and second spaced optical axes, respectively, aperture means having third and fourth optical axes, means for optically communicating the aperture and the first and second viewing means whereby the first and third axes form a viewing path and the second and fourth axes form another viewing path, the spacing between the third and fourth axes being less than the spacing between the first and second axes, and magnification means disposed along said viewing paths. Further in accordance with the invention in the embodiment described, the means for optically communicating the aperture and viewing means includes reflectors, and the system is mounted to be worn on the head.

According to the invention in a preferred embodiment thereof, a binocular stereoscopic magnification and illumination system is provided comprising first and second spaced viewing means having first and second spaced optical axes, respectively, aperture means having third and fourth optical axes, reflecting means for optically communicating the aperture and said first and second viewing means whereby the first and third axes form a viewing path and the second and fourth axes form another viewing path, the spacing between the third and fourth axes being less than the spacing between the first and second axes, magnification means disposed along said viewing paths, and means for projecting illuminating light through the aperture means along a fifth optical axis which is located intermediate or in close proximity to the third and fourth axes. The system is mounted on a head harness. The magnification means comprises first and second ocular means respectively located proximate the first and second viewing means, and objective means located proximate the aperture means. The ocular means are disclosed to be ocular lenses and the objective means a single objective lens. The ocular lenses are disclosed to be diverging lenses and the objective lens to be a converging lens, which cooperate to form Galilean-type telemicroscopes.

The means for optically communicating the aperture means and the viewing means are disclosed to be a plurality of reflective surfaces. The reflective surfaces are further disclosed to be front surface planar reflective surfaces spaced to provide periscope viewing from the first and second viewing means through the aperture means. A reflective surface is positioned adjacent each ocular lens and a corresponding reflective surface is positioned adjacent the objective lens. The means for projecting light comprises a fiber optics tube and another reflective surface positioned adjacent the objective lens, the fiber optics tube projecting light to the other reflective surface which reflects the light along the fifth optical axis. The reflective surfaces disposed adjacent the objective lens are disclosed to be off-plane, each being disposed as at least part of a side of a pyramid-type structure having its apex adjacent to and facing the objective lens. Further in accordance with the invention, each of the viewing means are adjustable to accommodate varying interocular distances.

These and other aspects of the invention will be more apparent from the following description of the preferred embodiments thereof when considered with the accompanying drawings and appended claims.

BRIEF DESCRIPTION OF THE DRAWINGS

The present invention is illustrated by way of example and not limitation in the figures of the accompanying drawings in which like references indicate similar parts and in which:

FIG. 1 is a perspective view depicting the binocular stereoscopic magnification and illumination system according to the invention mounted on a head harness and being used by a surgeon;

FIG. 2 is an enlarged front elevation view of the system of FIG. 1;

FIG. 3 is an exploded perspective view of the system of FIG. 1;

FIG. 4 is a schematic diagram depicting the optics of the system of FIG. 1;

FIG. 5 is a sectional view taken along lines 5—5 of FIG. 2;

FIG. 6 is a top view of the system of FIG. 1 depicting part of the optical portion of the system in section;

FIG. 7 is a schematic diagram depicting the optics of a prior art system;

FIG. 8 is a perspective view depicting the improved mounting means according to the invention for a surgical head lamp;

FIG. 9 is an enlarged front elevation view of the head lamp of FIG. 8; and

FIG. 10 is an enlarged side elevation view of the head lamp of FIG. 8.

DESCRIPTION OF THE PREFERRED EMBODIMENTS

Referring now to the drawings, a head-worn surgical illumination and binocular magnifying system 10 is illustrated. The head-worn system 10 depicted in FIG. 1 includes a head harness 12 which supports an optical system referenced generally by 14.

The head harness 12 includes an annular lower headband 18 and upper headband straps 20, 22. Channels 24 are secured to the sides of strap 22 which includes a pin that is insertable into one of holes 26 in strap 20, the channels and pin engaging and locking the overlapped straps. Lower headband 18 is cut at the rear and means are provided to adjustably engage the cut ends. Thus, the head harness 12 is fully adjustable. A soft, resilient material, preferably a plastic foam, is secured along the interior of the lower headband to provide cushioning. The head harness 12 is preferably made of a flexible, lightweight plastic material.

Illumination is supplied to the optical system 14 through a fiber optics tube 28 (FIG. 1). A fitting is secured to one end of the tube and is inserted in tubular opening 30 of optical system 14, the tube being maintained therein by, for example, a friction lock or an adhesive. The fiber optics tube is also adjustably secured to the upper straps and to the ends of the lower headband 18 by, for example, a pile lock in which the piles of overlapped members are interlocked upon the application of pressure to secure the tube 28 therebetween. The locks are released by pulling the pile members apart to separate them. The lock securing the tube to the upper straps is referenced by 32.

Referring more particularly now to FIG. 2, elements of the optical system 14 are disposed in a housing 34 which is secured to the head harness 12 by a plate 36, bracket 37 (FIG. 1) and hinge 38. The bracket 37 is secured to a tubular housing portion 42 which houses the aperture unit 43 of the optical system. The plate 36 is attached to the lower headband 18 by, for example, rivets. Hinge sections 39 are disposed on the plate 36 and mating hinge sections 40 are disposed on the bracket 37. A hinge pin 41 inserted through the mated hinge sections pivotably secures housing portion 42 to the plate 36. A helical spring disposed between an end of the pin and an outer hinge section urges the hinge sections together to cause a frictional engagement between the hinge sections. Accordingly, the optical system 14 may be adjustably positioned about the axis of pin 41 by overcoming the spring tension. Further details of the frictional hinge are shown in FIGS. 8–10 and described hereinafter. Arms 44 and 46 of housing 34 extend radially from housing portion 42. Housing 34, including arms 44 and 46 and housing portion 42, is generally hollow (FIGS. 5 and 6) and is fabricated from a lightweight material such as aluminum. Viewing units 48,50 (FIGS. 1 and 6) are adjustably connected to the ends of the arms 44 and 46 of the housing and project towards the surgeon's eyes. The optical unit 14 is suspended from plate 36 and additional support is provided by the nose bridge 52 of spectacles 54 via the spectacle frame and lenses and the viewing units 48,50 which contact the spectacle lenses 55. The spectacle lenses are conventional lenses, being plain or ground to suit the user's requirements. Alternatively, if a surgeon does not desire to wear spectacles, a nose bridge support may be provided for the optical unit.

Referring to FIGS. 3-6, the optical system includes an objective lens 56 disposed in the aperture unit 43, an ocular lens 58 disposed in each of the viewing units 48,50 and a periscope-type reflection system for optically communicating the objective lens and the ocular lenses. The reflection system comprises a central, pyramid-shaped reflector 62 having three front surface reflective planar surfaces 63, 64, 65 arranged as the sides of the pyramid, and a planar front surface reflector 68 disposed in each viewing unit along the optical axis of a respective ocular lens 58. The reflective surfaces of reflectors 62 and 68 are positioned between the corresponding ocular lens and the objective lens. The apex 66 of the pyramid is positioned along the central axis of the objective lens 56 and projects towards the objective lens. Ocular lenses 58 are double concave, i.e., they are negative or diverging lenses. The objective lens 56 is a double convex, converging lens. Light from the operating area 72 is converged by lens 56 to form images which are projected to reflective surfaces 63,64. The images are reflected to reflectors 68, which reflect the images to the ocular lenses 58. The ocular lenses magnify and focus the images at the retinas of the surgeon's eyes. Reflectors 68 and a respective reflective surface 63, 64, thus form respective periscopes. The combination of the objective lens 56 and the ocular lenses 58 operate as Galilean-type telemicroscopes and focus a magnified virtual image of the object (operating area) at the retinas of the surgeon's eyes.

Light conveyed through tube 28 is projected to reflective surface 65 and reflected therefrom through lens 56 which focuses the light at a focal point located in the operating area 72 to illuminate the area. The path of the light from the fiber optics tube 28 to the operating area is represented by the optical axes 74a, 74b. The paths of light from the operating area to the retinas are represented by optical axes 76a,b,c, and 78a,b,c. The reflective surfaces 63, 64 and 68 are positioned so that axes 76c and 78c are substantially parallel while axes 76a and 78a converge in the operating area.

Referring now to FIGS. 5 and 6, the objective lens 56, central reflector 62, ocular reflectors 68 and ocular lenses 58 are depicted mounted within the housing 34. A sleeve arrangement is utilized to mount the ocular lenses 58 in the housing. This arrangement comprises an externally threaded tubular inner sleeve 82 and an internally threaded outer tubular sleeve 84, the sleeves forming part of a respective viewing unit 48, 50. The inner sleeve projects through an opening 86 in each arm 44, 46 of housing 34 and the outer sleeve 84 is screwed onto the inner sleeve 82. The inner sleeve has an open end 88 and a closed end 90. The outer sleeve 82 includes an annular rib 92. The ocular lenses are slightly smaller diameter than the inner diameter of the outer sleeve 84. Thus, the ocular lens when placed within the outer sleeve is retained therein by the rib 92 and when the outer sleeve is screwed on the inner sleeve, the ocular lens is secured between the end 88 of the inner sleeve and the rib 92. This arrangement permits the ocular lenses to be easily inserted and removed from the viewing units. A similar sleeve arrangement is utilized to secure the objective lens to the viewing unit and comprises an outer internally threaded tubular sleeve 96 having an annular rib 98 and an inner internally threaded tubular sleeve 100.

Each reflector 68 is secured in a groove extending along the inner surface of the inner sleeve 82 and the end 90 of the sleeve. Each reflector 68 is circular and the groove is correspondingly annular. Resilient O-rings are disposed in the grooves to permit snap or press fitting of the reflectors into the grooves. The pyramid-shaped reflected 62 is snap-fitted into a triangular shaped groove 106 extending along the inner surface of the inner sleeve 100 and end 104. A resilient material is inserted into the triangular groove to provide a snap fit of the pyramid-shaped reflector into the groove. Each reflector 68 is mounted at approximately a 45° angle to the optical axis of the respective ocular lens and the reflective surfaces 63, 64 are mounted at approximately 45° angles with the optical axis of the objective lens. However, the lens angles at which reflectors 68 and reflective surfaces 63, 64 are positioned depends upon the distance at which it is desired that axes 76a and 78a converge to a point. Reflective surface 65 is positioned so that the axis of illumination 74b is between axes 76a and 78a and passes through or closely past the convergence point of axes 76a and 78a.

The inner sleeves 82 of the viewing units 48, 50 are adjustably mounted in respective arms 44, 46 of housing 34. A slotted opening 108 (FIG. 2) is provided in each arm and the openings 86 are enlarged so that each viewing unit is adjustable along the length of the slotted opening 108 to accomodate the interocular distances of individual surgeons. Each end 90 of the inner sleeves 82 has a threaded opening which receives the threaded shaft of a locking bolt 118 extending through the slotted openings. The viewing units 48, 50 are locked in position by tightening the locking bolts to draw ends 90 against the walls of arms 44,46. Adjustment is made by loosening the bolts, moving the viewing units laterally in the respective slotted openings to the desired position and then tightening the bolts again.

As mentioned, the optical unit 14 is pivotable about an axis extending through the pin 41 which secures the hinge sections of bracket 37 to those of plate 36. The tubular housing portion 42 is maintained in position by the spring tension exerted against the hinge sections. Housing 34 is continuously adjustable over a small angle of, for example, about 10° by overcoming the spring tension and pivoting the housing. Adjustment is provided to accomodate the physical features and facial contours of individual surgeons.

The particular lens system utilized is determined by such factors as the focal distances, resolution and magnification desired. For example, where high resolution is required, achromatic or aspheric lenses will be utilized. The precise distances between the lenses and the lens configuration or prescription will determine the magnification of the system. Such parameters are known or can be determined by those skilled in the art. As mentioned, the reflectors and reflective surfaces are of the front surface type. This is to minimize reflection errors. Additionally, it may be desirable to coat the lenses to reduce reflection therefrom. The lenses are preferably chosen so that the distance between the ocular lenses and the objective lens may remain constant. This permits simple replacement of the ocular and objective lenses to obtain varying magnification factors and focal distances.

The magnification system (ocular lenses 58 and objective lens 56) and the reflection system (reflectors 68 and reflector 62) are fixed in the system so that axes 76a and 78a and axis 74b are fixed with respect to one another. Thus, it is not necessary to adjust the optical unit during use to align the different axes. Therefore, the optical axes and illumination axis are always aligned.

The source of illumination is located to the rear of the surgeon with the illumination being conveyed by the fiber optics tube 28. The source may be a conventional projector-type bulb of 250 to 500 watts rating, for example. Such a source in combination with a fiber optics tube projects an intense, narrow beam of light to the optical system.

As mentioned, axes 76c and 78c are substantially parallel and axes 76a and 78a converge in the operating area. This enables the surgeon to look straight ahead as if he were focusing at infinity. The distance between axes 76a and 78a is substantially less than the distance between axes 76c and 78c. This has the effect of apparently reducing the interocular distance. Additionally, the angle A (FIG. 4) formed by axes 76c and 78c is small. The axis 74b of the light from the fiber optics tube 28 passes through or closely adjacent to the convergence point of axes 76a and 78a in the operating area. This enables the surgeon to stereoscopically look through a small opening 110 (FIG. 4) and along a narrow tube 112 to the operating area 72 while illuminating light is somewhat coaxially projected within the angle A formed by the optical axes (of vision) through the opening 110 and along the narrow tube 112. The inclination of reflectors 68 and reflective surfaces 62, 63 will determine the magnitude of angle A. As the magnification is increased, angle A may be decreased and the spacing between the axes 76a and 78a decreased.

While it is contemplated that a typical focal distance of the optical system will be about 16 inches, the usual range of use for the system is from about 8 to about 20 inches. Thus, the system may be used for a wide range of procedures having substantially different distances between the operating area and surgeon's eyes. Easy replacement of the lenses by unscrewing an outer sleeve, replacing the lens and then replacing the sleeve imparts versatility to an individual system in that a single system with a set of lenses can be used for many different surgical procedures.

Reflective surfaces 63, 64 and reflectors 68 form respective periscopes which reduce the apparent distance between the optical axes from the system to the operating area as described above whereby a surgeon's vision may be directed and focused through a small opening or in or at the end of a narrow passageway. The light from fiber optics tube 28 is reflected from surface 65 and has its optical axis 74b passing through or closely adjacent to the convergence point of the axes 76a and 78a. Thus, the projection of illuminating light to the operating area and the surgeon's field of vision overlap and are somewhat coaxial. This arrangement, which locates the axes of vision and the illumination optical axis within a small solid angle, permits the surgeon to view stereoscopically an illuminated operating area 74 of less than about 1½ inches in diameter which is located beyond a small opening or in or at the end of a narrow tube such as the auditory canal or nasal passage. This illuminated, stereoscopic vision is extremely difficult if not impossible using individual surgical telemicroscopes or loupes and fiber optics head lamps. Such a prior art system is depicted in FIG. 7. The optical axes 114, 116 through each telemicroscope 118, 120 are widely separated. Therefore it is not possible to both project light down the narrow tube 112 along the optical axis 122 of the fiber optics lamps 124 and at the same time view the operating area stereoscopically, i.e., with both eyes at the same time along the separate axes of vision. Thus, the operating area is usally viewed only by one eye and a loss of depth perception occurs. Additionally, slight movement of the surgeon's head may result in viewing of the operating area by a different eye and at times may possibly result in a complete loss of vision to the operating area. In contrast, since the axes of vision 76a and 78a are closely spaced according to the present invention, they are both always located within the narrow tube even with slight movement of the surgeon's head.

A Galilean-type telemicroscope is advantageous not only because the ocular lenses and objective lens may easily be replaced to obtain different focal distances, resolution and magnification, but also because an infinity focus ocular lens may be utilized. Such a lens is thin and when used in the system reduces the overall weight of the optical system. Additionally, the focal distance of the system having an infinity focus ocular lens is determined by the objective lens. Therefore, when employing infinity focus ocular lenses, the focal distance of the system may accordingly be changed by replacement of only the objective lens.

According to the embodiment shown in the drawings, a single objective lens is used for both ocular lenses of the Galilean telemicroscopes and also for focusing the light from the fiber optics tube. Thus, the number of lenses required is reduced, further reducing the weight of the optical system. Additionally, the single objective lens may be made larger than individual objective lenses thereby permitting more light to enter the optical system.

The ocular lenses are preferably made sufficiently large so that they may be spaced from the eyes. As a result, the ocular lenses may be positioned adjacent the lenses of spectacles obviating the need to mount the ocular lenses so that they will be in close proximity to the eyes, such as in the lenses of spectacles.

The system for reducing the interocular distance as described above is preferably a reflective system in order to still further reduce the weight of the optical unit 14. However, a refractive and a combined reflective-refractive system may also be used.

The lenses may be made from glass or plastic. Use of plastic will further reduce the weight of the optical system. If plastic lenses are employed, it is preferred that a plane lens be positioned adjacent each ocular lens and the objective lens on the exposed side thereof to protect them.

The magnifying system has been described to comprise ocular lenses and an objective lens. It is also within the contemplation of this invention that the magnifying system be a catadioptric system of a reflective system, i.e., magnification may be accomplished by one or more reflectors in lieu of a corresponding lens. For example, the central reflector may include curved reflective surfaces which function as reflective ocular pieces. Alternatively, the ocular reflectors may be curved to function as ocular pieces. This obviates the need for ocular lenses 58. Alternatively, the reflective surfaces of the central reflector 62 may be curved to function as objective pieces. In such an arrangement, the third surface of the central reflector is also curved to focus the light projecting from the fiber optics tube. The optical system may also comprise other combinations of lenses and reflectors. It is also contemplated that magnifying systems other than a two-lens Galilean system may be utilized.

The optical system described above is supported from head harness 12 by the hinged frictional lock 38 as described hereinbefore. A similar lock 126 shown in FIGS. 8–10 is used to support a fiber optics head lamp 128. The lock 126 includes a band or plate 36 having hinge sections 39, 39a formed at the bottom thereof. The plate is secured to headband 18 by riveting, for example. A bracket 37 is secured to the head lamp 128 and includes hinge sections 40, 40a are inserted between the hinge sections 39 of the plate. A hinge pin 41 is inserted through the openings of the hinge sections to pivotably connect the head lamp to the plate. The pin is slightly longer than the width of the plate and a coil spring 130 is disposed about the pin between one end 132 thereof and an end hinge section 40a of the head lamp bracket. The spring urges the end hinge sections 40a of the head lamp bracket 39a of the plate inwardly against inner hinge sections of the plate and head lamp bracket, respectively, to cause frictional engagement between the hinge sections of the plate and head lamp bracket. The hinge sections are somewhat resilient and are flexed inwardly under the spring tension. Adjustment of the head lamp is accomplished by overcoming the friction caused by the spring tension and pivoting the head lamp. The adjustment is continuous and may be done quickly, the head lamp being securely engaged in its adjusted position without the need to loosen and tighten screws or other fasteners.

While the present invention has been described with particular reference to the surgical field, it is to be understood that it it useful in other fields as well. For example, the invention may be used in medical fields such as dentistry and for medical examinations of, for example, the eyes, nose and ears. Additionally, the present invention may also be used in non-medical fields.

The advantages of the present invention, as well as certain changes and modifications of the disclosed embodiments thereof, will be readily apparent to those skilled in the art. It is the applicant's intention to cover by his claims all those changes and modifications which could be made to the embodiments of the invention herein chosen for the purpose of the disclosure without departing from the spirit and scope of the invention.

What is claimed is:

1. A head-worn binocular steroscopic viewing and illumination system comprising optical means and means for supporting said optical means, said means for supporting being adapted to being worn on a user's head, said optical means comprising first and second viewers spaced by a distance in a range corresponding to varying interocular distances, said viewers being adapted to being positioned adjacent to the eyes of a user, means for projecting light, an aperture common to said first and second viewers and said light projecting means and optically coupled thereto for viewing and projecting light through the aperture, first and second reflective surfaces disposed to provide an optical path between said first viewer and said aperture, third and fourth reflective surfaces disposed to provide an optical path between said second viewer and said aperture, and a fifth reflective surface disposed to provide an optical path between the light projecting means and said aperture, said second, fourth and fifth reflective surfaces being adjacently disposed such that respective optical paths from the second, fourth and fifth reflective surfaces to the common aperture are closely spaced.

2. The system recited in claim 1, and including a generally hollow housing, said viewers being disposed on one side of said housing and said aperture on the side of said housing opposed to said one side.

3. The system recited in claim 1, wherein each of said viewers are adjustable to accomodate varying interocular distances.

4. The system recited in claim 1, wherein said means for supporting comprises a head harness adapted to fit a user's head and said means for securing said optical means to said head-worn means comprises frictionally engaged hinge means operative to permit movement of said optical means.

5. The system recited in claim 1, wherein said second, fourth and fifth reflective surfaces extend off-plane with respect to each other and have converging sides which are adjacently disposed.

6. The system recited in claim 1, wherein said second, fourth and fifth reflective surfaces each have converging sides which meet in a vertex, the vertices of said second, fourth and fifth reflective surfaces being disposed at a common point facing said aperture.

7. The system recited in claim 1, wherein said light projecting means includes a fiber optics tube which projects light towards said fifth reflective surface.

8. The system recited in claim 1 and comprising magnification means which comprises first and second ocular means respectively located proximate said first and second viewers and a single objective common to said first and second ocular means located proximate said aperture.

9. The system recited in claim 8, wherein said first and second ocular means respectively comprise first and second ocular lenses and said single objective comprises an objective lens.

10. The system recited in claim 9, wherein each of said first and second ocular lenses are diverging lenses and said objective lens is a converging lens, said first ocular lens and said objective lens, and said second ocular lens and said objective lens cooperating to form Galilean-type telemicroscopes.

11. The system recited in claim 9, wherein the ocular lenses are infinity focus lenses, the focal distance of the system being determined by the objective lens.

* * * * *

UNITED STATES PATENT AND TRADEMARK OFFICE
CERTIFICATE OF CORRECTION

PATENT NO. : 4,196,966
DATED : April 8, 1980
INVENTOR(S) : Leonard I. Malis

It is certified that error appears in the above—identified patent and that said Letters Patent is hereby corrected as shown below:

Column 5, line 59 - after "are" insert --of--

Column 6, line 52 - change "distances" to --distance--

Column 7, line 61 - change "74" to --72--

Column 8, line 7 - change "usally" to --usually--

Column 8, line 7 - change "only by" to --by only--

Column 8, line 57 - change "of" to --or--

Column 9, line 13 - after "40a" insert --which--

Column 9, line 49 - change "steroscopic" to --stereoscopic--

Signed and Sealed this

Nineteenth Day of August 1980

[SEAL]

Attest:

SIDNEY A. DIAMOND

Attesting Officer     Commissioner of Patents and Trademarks